United States Patent [19]

Pasky

[11] 4,451,689

[45] May 29, 1984

[54] CO-DIMERIZATION OF OLEFINS

[75] Inventor: Joseph Z. Pasky, Novato, Calif.

[73] Assignee: Chevron Research Company, San Francisco, Calif.

[21] Appl. No.: 402,492

[22] Filed: Jul. 27, 1982

[51] Int. Cl.$^3$ .............................................. C07C 3/02
[52] U.S. Cl. .................................. 585/525; 585/329; 585/510; 585/532
[58] Field of Search ............... 585/329, 511, 512, 521, 585/522, 525, 510, 530, 532

[56] References Cited

U.S. PATENT DOCUMENTS

| | | | |
|---|---|---|---|
| 4,263,465 | 4/1981 | Sheng et al. | 585/329 |
| 4,317,948 | 3/1982 | Heckelsberg | 585/329 |
| 4,319,064 | 3/1982 | Heckelsberg et al. | 585/329 |

FOREIGN PATENT DOCUMENTS 576759  5/1959  Canada .............................. 585/511

*Primary Examiner*—Delbert E. Gantz
*Assistant Examiner*—A. Pal
*Attorney, Agent, or Firm*—S. R. La Paglia; T. G. De Jonghe; C. J. Caroli

[57] ABSTRACT

Preparation of high molecular weight, branched-chain olefins by the co-dimerization of $C_9$–$C_{21}$ branched-chain internal olefins by a process comprising (a) contacting a propylene oligomer feedstock having from 9 to 21 carbon atoms in a reaction zone with a catalyst selected from the group consisting of hydrogen fluoride, boron trifluoride-alkanol and aluminum chloride; (b) maintaining the temperature in the reaction zone between about 0° C. and 75° C.; and (c) maintaining the pressure in the reaction zone between about 0 psig and 100 psig.

7 Claims, No Drawings

CO-DIMERIZATION OF OLEFINS

BACKGROUND OF THE INVENTION

The present invention relates to a process for the preparation of high molecular weight, branched-chain olefins by the co-dimerization of $C_9$–$C_{21}$ branched-chain internal olefins in the presence of an acid catalyst.

The dimerization of alpha olefins is known in the art. Thus, U.S. Pat. No. 2,830,106 describes the dimerization of alpha olefins having from 6 to 15 carbon atoms utilizing a solid catalyst consisting of activated alumina containing about 0.5% to 3% by weight hydrogen fluoride. Suitable olefin feeds described in this patent are those having no alkyl side chains or which are only slightly branched, particularly normal alkenes.

Similarly, U.S. Pat. No. 4,205,195 describes the dimerization of alpha olefins having from 8 to 20 carbon atoms in the presence of hydrofluoric acid. In particular, this patent shows the dimerization of straight-chain olefins having a terminal double bond, preferably alpha olefins of 10 to 16 carbon atoms.

SUMMARY OF THE INVENTION

It has now surprisingly been found that the production of $C_{18}$–$C_{42}$ branched-chain olefins is successfully achieved by the co-dimerization of $C_9$–$C_{21}$ branched-chain internal olefins by a process which comprises (a) contacting a propylene oligomer feedstock having from 9 to 21 carbon atoms in a reaction zone with a catalyst selected from the group consisting of hydrogen fluoride, boron trifluoride-alkanol and aluminum chloride; (b) maintaining the temperature in the reaction zone between about 0° C. and 75° C.; and (c) maintaining the pressure in the reaction zone between about 0 psig and 100 psig.

Among other factors, the present invention is based on the discovery that $C_9$–$C_{21}$ internal olefins which are also highly branched can be co-dimerized to provide high molecular weight branched-chain olefins in high yield and conversions.

The process of the present invention is suitable for the production of $C_{18}$–$C_{42}$ branched-chain olefins. The olefins thus prepared are highly branched compounds and the term "branched-chain" is herein used to signify at least one carbon branch per every three carbon atoms in the olefin product.

A propylene oligomer feedstock having from 9 to 21 carbon atoms and an internal double bond is used as the starting material. This feedstock may be obtained by the direct oligomerization of propylene in an acid medium. Preferred feedstocks include those containing from about 12 to 18 carbon atoms.

The propylene oligomer feedstock is then contacted with an acidic catalyst selected from hydrogen fluoride, boron trifluoride-alkanol and aluminum chloride. The reaction is carried out at a temperature of about 0° C. to about 75° C., preferably from about 0° C. to about 70° C. The reaction pressure is maintained at about 0 psig to about 100 psig, preferably from about 0 psig to about 50 psig.

The use of hydrogen fluoride, boron trifluoride and aluminum chloride as co-dimerization catalysts has been found to be satisfactory for providing the olefin co-dimer in high yield. When hydrogen fluoride is the catalyst, about 5 to 10, and preferably about 6 to 8, moles of hydrogen fluoride are utilized per mole of olefin feedstock. The hydrogen fluoride catalyzed reaction proceeds to give about 65% conversion to the co-dimerized product. Removal of fluoride from the co-dimerized product can be accomplished by conventional means, such as distillation.

When boron trifluoride is the catalyst, it is preferably utilized in combination with an alkanol. Suitable alkanols include straight-chain alkanols of 1 to 8 carbon atoms. A preferred alkanol is n-butanol. Generally, about 0.05 to 1.0, preferably about 0.1 to 0.3, moles of boron trifluoride are utilized per mole of olefin feedstock. The boron trifluoride-alkanol catalyzed reaction proceeds to give over 60% conversion to the co-dimerized product.

With an aluminum chloride catalyst, about 0.05 to 1.0, and preferably about 0.1 to 0.3, moles of aluminum chloride are utilized per mole of olefin feedstock. The reaction may also be carried out in the presence of an alkanol, such as n-butanol. The aluminum chloride catalyzed reaction proceeds to give over 50% conversion to the co-dimerized product.

The co-dimerized branched-chain olefinic products may be separated from the reaction mixture by conventional procedures, such as fractional distillation.

The $C_{18}$–$C_{42}$ branched-chain olefins prepared by the process of the present invention are useful as precursors for surface-active products, lubricating compositions, and the like.

The following examples are provided to illustrate the invention in accordance with the principles of the invention but are not to be construed as limiting the invention in any way except as indicated by the appended claims.

EXAMPLES

Example 1

To a 2-liter, 3-necked flask provided with a gas inlet tube, stirrer, thermometer and condenser, there was placed 1600 ml (1272 g, 5.5 moles) of a 50/50 mixture of $C_{15}$ and $C_{18}$ propylene oligomers. While maintaining the solution saturated with boron trifluoride, n-butanol was added over a period of 2.5 hours. Thirty minutes after the n-butanol addition was started, the reaction mixture was heated to 60° C. Samples were taken for analysis at 0.5, 2 and 3 hours. The results are shown in Table 1.

TABLE 1

| Time, hours | Olefin Conversion | Moles of Catalyst[1] ($BF_3$/n-butanol) | Moles of Catalyst per Moles of Olefin |
| --- | --- | --- | --- |
| 0.5 | 23% | 0.35 | 0.067 |
| 2 | 53% | 1.6 | 0.3 |
| 3 | 64% | 2.4 | 0.46 |

[1]Calculated on basis of total n-butanol added.

Example 2

A 500-ml flask was equipped with a stirrer, thermowell, condenser, heating mantle, and dropping funnel. Approximately 300 ml (231 g, 1.2 moles) of a mixture of $C_{12}$ and $C_{15}$ propylene oligomers was placed in the flask and 25 ml (34.5 g, 0.26 moles) of an $AlCl_3$.n-butanol catalyst (1:1) was added over a period of 50 minutes. The temperature was raised to about 60° C. over the next 1.5 hours and held at this temperature for another hour while an additional 25 ml of catalyst solution was added. Approximately 5 ml of sample were periodically withdrawn, quenched with 10% HCl and the hydrocarbon analyzed by gas chromatography. The results are shown in Table 2.

TABLE 2

| Time, minutes | Temperature, °C. | Olefin Conversion |
|---|---|---|
| 30 | 29 | 1.5% |
| 71 | 55 | 7.7% |
| 113 | 60 | 26% |
| 153 | 60 | 39% |
| 208 | 61 | 47% |
| 253 | 61 | 52% |
| 313 | 61 | 55% |

Example 3

To a 1000-ml polypropylene bottle equipped with stirrer, thermowell, condenser, dropping funnel, and sample port, 250 ml (12.0 moles) of hydrogen fluoride was added. The reaction vessel was immersed in an acetone-ice bath, and 500 ml of a hydrocarbon consisting of 250 ml (195 g, 0.93 moles) of a $C_{15}$ propylene oligomer and 250 ml (200 g, 0.79 moles) of a $C_{18}$ propylene oligomer were added over a period of an hour. Samples taken periodically were quenched in aqueous KOH and analyzed by gas chromatography. After 2.5 hours, olefin conversion was 55% to a co-dimerized product having a carbon range of $C_{28}$–$C_{42}$ and an average carbon number of $C_{33}$.

The above experiment was repeated with a mixture of a $C_{12-15}$ propylene oligomer and a $C_{18}$ propylene oligomer. After 6 hours, olefin conversion was 65% to a co-dimerized product having a carbon range of $C_{24}$–$C_{40}$ and an average carbon number of $C_{30}$.

What is claimed is:

1. A process for the preparation of $C_{18}$–$C_{42}$ branched-chain olefins by the co-dimerization of $C_9$–$C_{21}$ branched-chain internal olefins which comprises:
    (a) contacting a low molecular weight propylene oligomer feedstock having from 9 to 21 carbon atoms in a reaction zone with a catalyst selected from the group consisting of hydrogen fluoride, and aluminum chloride;
    (b) maintaining the temperature in the reaction zone between about 0° C. and 75° C.; and
    (c) maintaining the pressure in the reaction zone between about 0 psig to about 100 psig.
2. A process according to claim 1, wherein the catalyst is hydrogen fluoride.
3. A process according to claim 1, wherein the catalyst is aluminum chloride.
4. A process according to claim 1, wherein the reaction is carried out at a temperature between about 0° C. and 70° C.
5. A process according to claim 1, wherein the reaction is carried out at a pressure between about 0 psig and 50 psig.
6. A process according to claim 1, wherein the propylene oligomer feedstock contains from 12 to 18 carbon atoms.
7. A process according to claim 1, wherein the reaction zone reaction conditions are maintained sufficient to yield at least 50% conversion of the $C_9$–$C_{21}$ branched-chain internal olefins to the $C_{18}$–$C_{42}$ branched-chain olefins, including a temperature between about 0° C. and 75° C. and a pressure between about 0 psig and 100 psig.

* * * * *